(12) United States Patent
Kurata et al.

(10) Patent No.: US 6,650,922 B2
(45) Date of Patent: Nov. 18, 2003

(54) BIOLOGICAL ELECTRODE

(75) Inventors: Tohru Kurata, Tokyo (JP); Shin Suda, Tokyo (JP)

(73) Assignee: Nihon Kohden Corporation, Tokyo (JP)

(*) Notice: Subject to any disclaimer, the term of this patent is extended or adjusted under 35 U.S.C. 154(b) by 46 days.

(21) Appl. No.: 09/833,813

(22) Filed: Apr. 13, 2001

(65) Prior Publication Data

US 2001/0031988 A1 Oct. 18, 2001

(30) Foreign Application Priority Data

Apr. 13, 2000 (JP) .................................. P. 2000-112313

(51) Int. Cl.[7] .............................................. A61B 5/04
(52) U.S. Cl. ...................... 600/395; 600/396; 607/149; 607/152; 607/153
(58) Field of Search .................................. 600/372, 395, 600/396; 607/115, 119, 122, 149, 152, 153

(56) References Cited

U.S. PATENT DOCUMENTS

| 4,102,331 A | * | 7/1978 | Grayzel et al. | ............. | 600/397 |
| 4,444,206 A | * | 4/1984 | Gold | ........................ | 607/126 |
| 4,506,673 A | * | 3/1985 | Bonnell | ...................... | 607/50 |
| 5,370,115 A | | 12/1994 | Ogawa et al. | .............. | 128/639 |
| 6,095,148 A | * | 8/2000 | Shastri et al. | ............... | 607/116 |
| 6,463,335 B1 | * | 10/2002 | Munch et al. | ............... | 600/374 |

* cited by examiner

Primary Examiner—Lee Cohen
(74) Attorney, Agent, or Firm—Sughrue Mion, PLLC

(57) ABSTRACT

A biological electrode includes an electrode element having electroconductivity with respect to a living body, the biological electrode used by disposing said electrode element at a predetermined position, and the electrode element being made of biodegradable material.

11 Claims, 3 Drawing Sheets

BIOLOGICAL ELECTRODE

BACKGROUND OF INVENTION

1. Field of Invention

The present invention relates to a biological electrode, and more particularly to a biological electrode which is suitably used for the bioelectrical monitoring and/or bioelectrical stimulation by disposing an electrode element capable of having electroconductivity with a living body at a predetermined position.

2. Related Art

Conventionally, for the bioelectrical monitoring and/or bioelectrical stimulation for the medical and/or biological purposes, the measurement was conducted by attaching a biological electrode at a predetermined position of a living body.

The biological electrodes are roughly classified into a disposable type and a re-usable type.

A re-usable biological electrode is durable, and thus rarely wasted, with less risk of bringing about a significant waste problem.

In recent years, a disposable biological electrode has been more and more used to avoid infection. Since a large quantity of disposable biological electrodes are used and wasted, and the material that is less degradable in the natural environment is employed, there is a risk of causing a waste problem such as insufficient garbage dump.

The conventional structure of an electrode element for use with the disposable biological electrode can be roughly classified into two types as follows.

The first type is a so-called snap fastener type in which the electrode element is connected via a snap connector to the lead wire.

The second type is a so-called film element type in which the electrode element is like a film, with its one end being connected via an alligator clip to the lead wire, for example.

In FIG. 6, a biological electrode 41 comprises a snap fastener type element 42, an adhesive tape 43, a gel sponge 44, and an electrode paste 45 or the like, and is used as a disposable electrode for the electrocardiogram monitor, for example.

Conventionally, as the material of the disposable biological electrode 41, ABS resin (acrylonitrile butadiene styrene copolymer) was employed for the snap fastener type electrode element 42. The electrode element 42 is made electroconductive by kneading an electroconductive filler such as carbon into ABS resin or by coating an electroconducitve paint on its surface to form an electroconductive layer. Also, a non-polarized electroconductive paint such as silver/silver chloride paint is coated on the contact face of the electrode paste 45 on the electrode element 42, as required, to give a stable performance to the electrode element 42 of the biological electrode 41.

Further, the contact between the electrode element 42 and a connecting terminal of the electrode lead wire is improved by coating a highly electroconducitve paint on a lead wire attaching portion of the electrode element 42, or by putting a stainless cover (e.g., a stud) thereon.

On the other hand, a biological electrode 50 of film element type has an electroconductive layer 53 that is formed by coating an electroconducitve paint such as silver/silver chloride paint on at least a part of one face of a substrate 52 made of PET resin (polyethylene terephthalate) or the like, and an electroconductive gel 54 fixedly provided with the electroconductive layer 53, as shown in FIG. 7. And the biological electrode 50 is employed as a disposable electrode for electrocardiography, for example.

A large quantity of disposable biological electrodes are used for the purposes of the electrode for electrocardiogram monitoring in the ward, or the tab electrode for group medical checkup making use of the electroconductive adhesive gel, and also wasted.

Of the materials used in the biological electrode 41 as shown in FIG. 6, the electrode element 42 in particular is made of ABS resin, and in an embodiment as shown in FIG. 7, the substrate 52 in particular is made of PET resin. Therefore, in an incinerating process, a large amount of heat is generated while incinerating, whereby there is a drawback that an incinerator is easily damaged.

In the garbage dump after the use, the noncombustible waste is less liable to degrade in the natural environment, when wasted, and remains in the environment over the long term without degrading in the soil. Therefore, it is apprehended that the lifetime of the garbage dump or final repository site may be shortened, thereby causing some load on the natural environment.

SUMMARY OF INVENTION

The present invention has been achieved in the light of the above-mentioned problems, and it is an object of the invention to provide a biological electrode that causes less natural environmental load, even if wasted in large quantities in the soil, or generates a small heat amount while incinerating, not damaging the incinerator.

The first invention provides a biological electrode comprising at least an electrode element capable of having electroconductivity with a living body, the biological electrode being used by disposing the electrode element at a predetermined position, wherein a biodegradable material is used in the electrode element of the biological electrode.

Accordingly, according to the invention, the use of a biodegradable material for the biological electrode can not only retain the electrochemical performance and mechanical performance, but also can be degradable into the water and carbon dioxide ultimately owing to microbes, when wasted in the soil.

In the incineration process, the biological electrode of the invention generates a smaller amount of heat while incinerating than the conventional electrode made of ABS resin or PET resin.

The second invention provides the biological electrode, wherein the biodegradable material contains a material selected from at least one of cellulose, polyhydroxy carboxylic acids, chitosan, aliphatic polyester (e.g., polybutylenesuccinate (PBS), polybutylenesuccinate adipate (PBSA), polyethylenesuccinate (PESu)), polycaprolactone (PCL), and starch derivatives. Therefore, the biological electrode of the invention is degradable into the water and carbon dioxide ultimately owing to microbes, and generates a small amount of heat while incinerating in the incineration process.

The third invention provides the biological electrode, wherein an electroconductive filler is specifically added to a matrix of the electrode element to afford the electroconductivity.

The fourth invention provides the biological electrode, wherein an electroconductive layer is specifically formed on the surface of a matrix or substrate of the electrode element to afford the electroconductivity.

The fifth invention provides the biological electrode, wherein the substrate is a non-woven fabric made of the biodegradable material. The substrate composed of the non-woven fabric is so flexible as to reduce delamination or uncomfortableness in attaching, with excellent air permeability, and has the functions of low heat generation while incinerating and degradation in the soil with the garbage disposal after the use.

The sixth invention provides the biological electrode, further comprising a pad portion which is a non-woven fabric made of the biodegradable material. The pad portion composed of the non-woven fabric is so flexible as to reduce delamination or uncomfortableness in attaching, with excellent air permeability, and has the functions of low heat generation while incinerating and degradation in the soil with the garbage disposal after the use.

The seventh invention provides the biological electrode, wherein the biodegradable materials contains a material selected from at least one of cellulose, polyhydroxy carboxylic acids, chitosan, aliphatic polyester (e.g., polybutylenesuccinate (PBS), polybutylenesuccinate adipate (PBSA), polyethylenesuccinate (PESu)), polycaprolactone (PCL), and starch derivatives. Thereby, it is possible to have the superior functions of low heat generation while incinerating and degradation in the soil.

The eighth invention provides the biological electrode, wherein the biodegradable material is used for all the constituent members of the biological electrode.

The ninth invention provides a method of manufacturing an electrode element of a biological electrode, characterized by including a step of kneading a biodegradable material as a matrix and an electroconductive filler, and a step of injection molding after kneading.

The tenth invention provides a method of manufacturing an electrode element of a biological electrode, characterized by including a step of coating or infiltrating an electroconductive paint on a film or a non-woven fabric made of a biodegradable material as a substrate.

DETAILED DESCRIPTION OF PREFERRED EMBODIMENTS

The preferred embodiments of the present invention will be described below with reference to the drawings.

Figure 1:
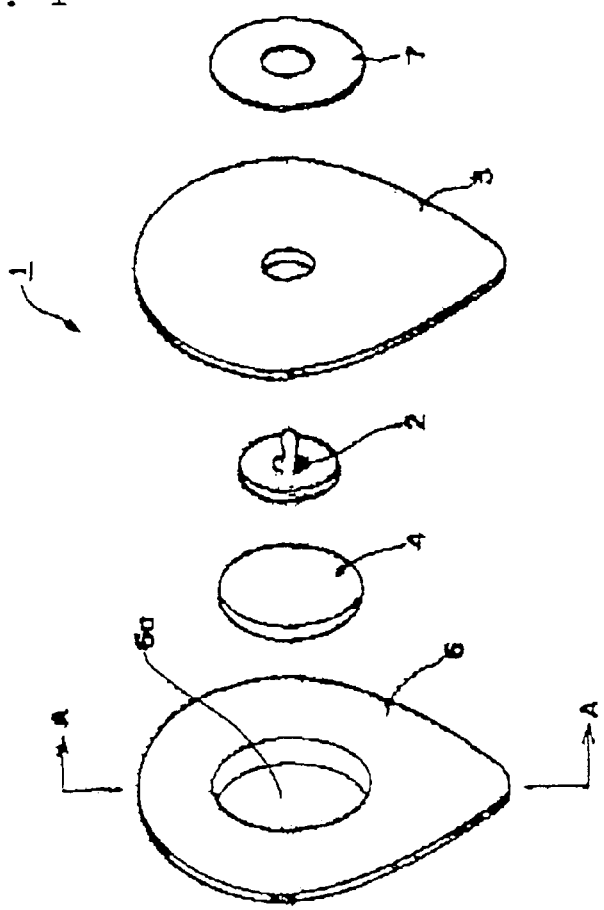
FIG. 1 is a schematic perspective view illustrating a first embodiment of a biological electrode 1 according to the present invention.

FIG. 1 is a schematic perspective view illustrating a first embodiment of a biological electrode according to the invention.

Figure 2:
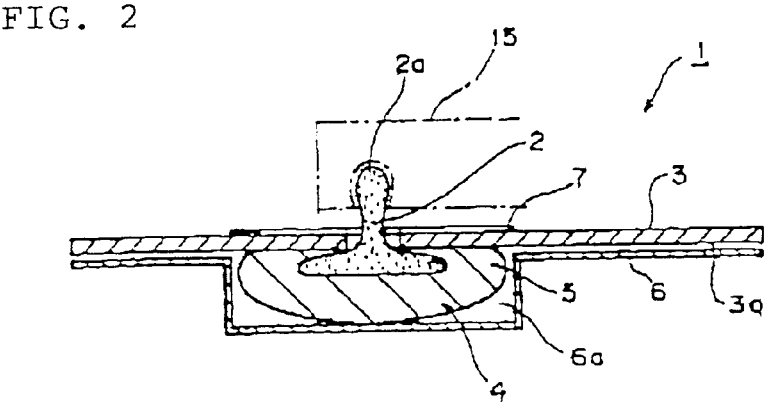
FIG. 2 is a cross-sectional view illustrating a portion of the biological electrode as shown in FIG. 1, taken along the line A—A.

FIG. 2 is a cross-sectional view of the essence of the biological electrode as shown in FIG. 1.

Figure 3:
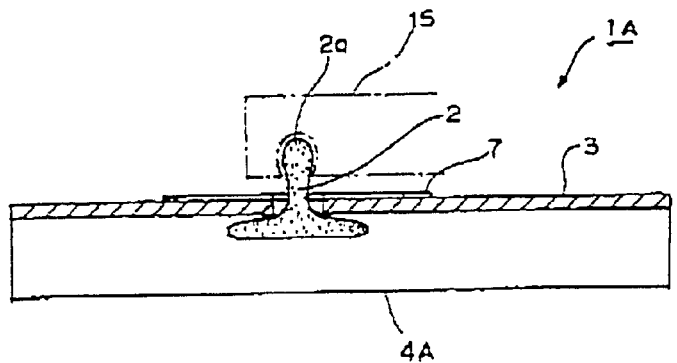
FIG. 3 is a cross-sectional view in essence illustrating a variation of the first embodiment of the biological electrode according to the invention.

FIG. 3 is a cross-sectional view illustrating the essence of a variation of the biological electrode as shown in FIG. 2.

Figure 4:
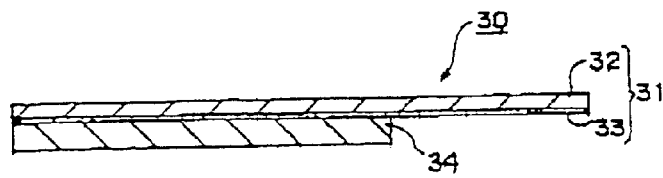
FIG. 4 is a cross-sectional view in essence illustrating a second embodiment of a biological electrode according to the invention.
Figure 5:
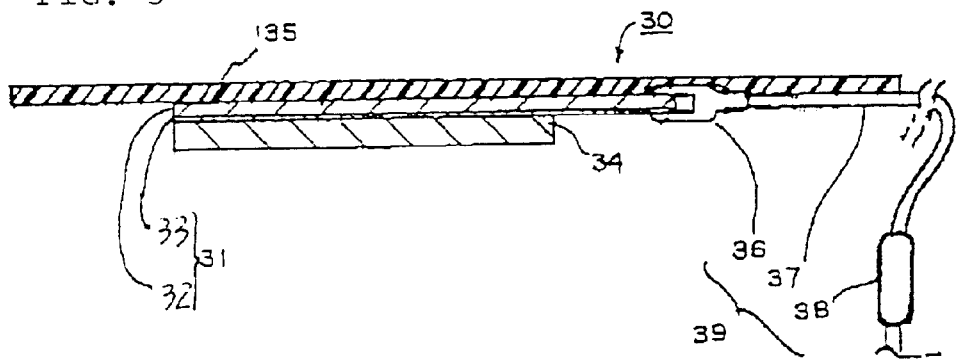
FIG. 5 is a schematic cross-sectional view in essence illustrating a variation of the second embodiment of the biological electrode according to the invention.
Figure 6:
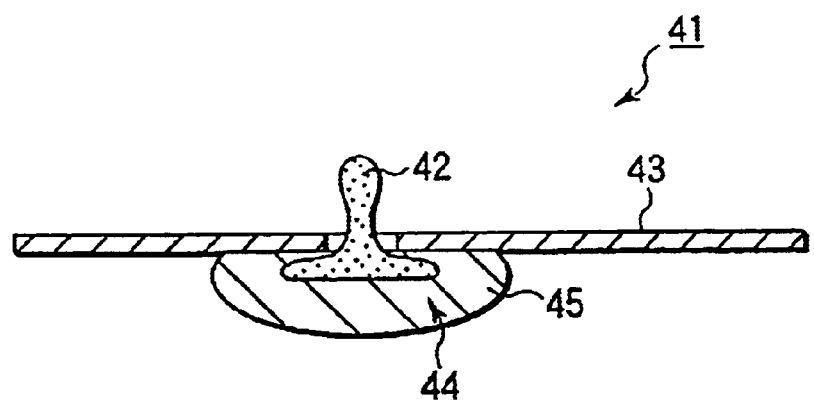
FIG. 6 is a cross-sectional view of the conventional biological electrode.
Figure 7:
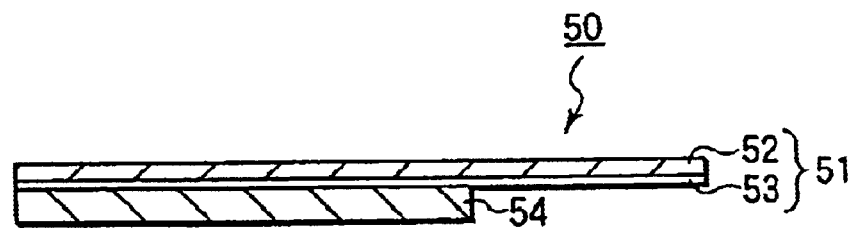
FIG. 7 is a cross-sectional view of the conventional biological electrode.

FIGS. 4 and 5 are cross-sectional views illustrating a second embodiment of the biological electrode according to the invention.

First Embodiment

As shown in FIGS. 1 and 2, the biological electrode 1 of this embodiment is disposable, and comprises an electrode element 2 capable of having electroconductivity with a living body, a sponge with electroconductive gel 4 on a flat side of the electrode element 2 or on a contact face with the living body (a lower side in the figure), and a pad portion 3 having an adhesive face 3a on a clavate side of the electrode element 2. This biological electrode 1 is placed at a predetermined position of the living body owing to adhesion of the adhesive face 3a of the pad portion 3. The electrode element 2 is clavate at a top end 2a, and has a snap fastener type structure of fitting with a concave portion of a connecting part 15 for the lead wire, as shown in FIG. 2, for example.

And in this embodiment, of the constituent members of the biological electrode 1, the electrode element 2 is formed of a biodegradable material. Because this sponge with gel 4 serves to make close contact with the living body, the electrode element 2 can be disposed securely at a predetermined position by the pad portion 3 having adhesion. The sponge with gel 4 does not remain on the skin when peeled from an attached portion, and is unnecessary to wipe out, improving the usability of the biological electrode 1.

In this embodiment, a gel cover 6 having a concave portion 6a for protecting the sponge with gel 4 and covering the adhesive face of the pad portion 3 is provided. This gel cover 6 prevents the gel from drying over the long time before the biological electrode 1 is used, and further protects the sponge with gel 4 and keeps adhesion of the pad portion 3 for the long term. A label 7 can secure the electrode element 2 firmly, and suppress the noise due to movement of the lead wire to the minimum.

The electrode element 2 is formed of at least one kind of biodegradable material from among polyhydroxy carboxylic acids such as polylactic acid and polyglycolic acid, chitosan, cellulose, aliphatic polyester (e.g., polybutylenesuccinate (PBS), polybutylenesuccinate adipate (PBSA), polyethylenesuccinate (PESu)), polycaprolactone (PCL), and starch derivatives. Therefore, the electrode element 2 can attain a mechanical performance and is ultimately decomposed into water and carbon dioxide by soil microbes, with the small amount of heat generated in incineration. In particular, the use of polylactic acid can prevent the electrode element from molding.

Also, the electrode element 2 is molded by adding an adequate amount of electroconductive material to the biodegradable material, and provided with some electrochemical property. Also, an electroconductive layer composed of an electroconductive material may be formed on the biodegradable material.

The electroconductive materials may include, for example, silver, silver/silver chloride, or carbon.

The biological electrode 1 thus constituted is finally decomposed into water and carbon dioxide owing to microbes, when wasted in the soil after the use. Also, in the incineration process, it generates the smaller amount of heat while incinerating than the conventional biological electrode using ABS resin or PET resin.

The biodegradable materials in this embodiment will be detailed below.

As the biodegradable materials in this embodiment, polyhydroxy carboxylic acids such as polylactic acid are a generic name of the following substances. These substances may be used singly as raw materials or in mixture thereof. For example, lactide that is a cyclic ester of L-lactic acid, D-lactic acid, DL-lactic acid, or lactic acid may be used.

The materials that can form a copolymer with lactic acid may include hydroxy carboxylic acids such as glycolic acid, 3-hydroxybutyric acid, 4-hydroxybutyric acid, 4-hydroxy valeric acid, and 6-hydroxy carboxylic acid. Further, the cyclic ester of hydroxy carboxylic acids may be glycolide (cyclic ester of glycolic acid), or $\epsilon$-caprolactone (6-cyclic ester of hydroxy caproic acid).

By polymerizing the raw materials as above cited, polyhydroxy carboxylic acids such as high molecular polylactic acid can be obtained. In polymerization, direct dehydroxy polycondensation from hydroxy carboxylic acids or ring opening polymerization from ringular dimer of hydroxy carboxylic acids (e.g. lactide) can be used in accordance with the properties of raw material.

A method of manufacturing a snap fastener type (FIGS. 1 and 2) electrode element in this embodiment (kneading electroconductive material) will be described below.

1) Kneading the biodegradable material and the electroconductive filler;

The biodegradable material of polyhydroxy carboxylic acid such as polylactic acid is used as the matrix of the electrode element 2.

By kneading and adding the electroconductive filler into the matrix, the biological electrode 1 is provided with electroconductivity.

The electroconductive fillers include carbon black, silver, and silver/silver chloride.

Carbon black may be acetylene black or furnace black.

The electroconductive filler is in pulverulent form.

Means for kneading the electroconductive filler into biodegradable material may include a Henschel mixer, a ribbon blender, a mill roller, a Bambari mixer, a super mixer, and a single or twin extruder.

When kneading the electroconductive filler,

The additive amount of electroconductive filler is in a range of 15 to 40 percent for carbon black, and 30 to 80 percent for silver and silver/silver chloride, supposing 100 percent in total.

The surface resistivity after kneading is in a range of $1 \times 10^5$ ($\Omega$) or less.

2) Shaping the electrode element 2;

The injection molding conditions (injection temperature, mold temperature) after kneading may be in the most suitable range of matrix.

For example, when polylactic acid is used for the matrix, the injection temperature may be in a range from 100 to 300° C., and the mold temperature may be in a range from 10 to 80° C.

3) Coating the electroconductive paint onto the lead wire attaching portion of the electrode element 2;

Separately from or simultaneously with kneading the electroconductive filler to provide the electroconductivity, a highly electroconductive part is formed on the surface by coating an electroconductive paint on a lead wire attaching portion of the element, if necessary, thereby improving the electrical contact with the lead wire.

Further, a stainless cover (e.g., stud) may be provided on the lead wire attaching portion of the electrode element 2, thereby improving the electrical contact between the electrode element 2 and the connecting terminal of the electrode lead wire.

4) Coating the non-polarized elecroconductive paint on the electrode paste contact face of the electrode element 2;

To further enhance the performance of the biological electrode 1, an electroconductive paint of silver/silver chloride as the electroconductive material may be coated at a portion in contact with the electrode paste or the electrode gel on the electrode element 2 having electroconductivity, if necessary.

5) Standards;

The electrode performance of the biological electrode 1 after assembly must satisfy the standard, AAMI/ANSI-EC-12: Pregelled ECG Disposable Electrodes (1982) that have standardized test items such as AC impedance, DC offset voltage, DC offset drift, defibrillation overload recovery, and Bias current tolerance.

(3) A manufacturing method of the snap fastener type electrode element 2 (with the electroconductive paint coated on the surface to form an electroconductive layer)

1) Molding the electrode element 2

The injection molding conditions (injection temperature, mold temperature) may be in the most suitable range of the matrix.

For example, when polylactic acid is used for the matrix, the injection temperature may be in a range from 100 to 300° C., and the mold temperature may be in a range from 10 to 80° C.

2) Coating the electroconductive paint on the surface of the electrode element 2;

The kinds of electroconductive material to be added to the electroconductive paint include carbon black, silver, and silver/silver chloride.

Carbon black may be acetylene black or furnace black.

The surface resistivity after coating is $1 \times 10^5$ ($\Omega$) or less.

For coating an electroconductive paint, the suitable methods such as vapor deposition, plating, spray coating, screen printing, and hot melt can be taken in accordance with the characteristics of the paint.

3) Coating the electroconductive paint on the lead wire attaching portion of the electrode element 2;

Simultaneously with coating the electroconductive paint to provide the electroconductivity, a highly electroconductive part is particularly formed on the surface by coating another kind of electroconductive paint on the lead wire attaching portion of the electrode element, if necessary, thereby improving the electrical contact with the lead wire.

For coating an electroconductive paint, the suitable methods such as vapor deposition, plating, spray coating, screen printing, and hot melt can be taken in accordance with the characteristics of the paint.

Further, a stainless cover (e.g., stud) may be provided on the lead wire attaching portion of the electrode element 2, thereby improving the electrical contact between the electrode element 2 and the connecting terminal of the electrode lead wire.

4) Coating the non-polarized elecroconductive paint on the electrode paste contact face of the electrode element 2;

To further enhance the performance of the electrode element 2 of the biological electrode 1, an electroconductive paint of silver/silver chloride as the electroconductive material may be coated at a part in contact with the electrode paste or the electrode gel on the electrode element 2 having electroconductivity, if necessary.

For coating an electroconductive paint, the suitable methods such as vapor deposition, plating, spray coating, screen printing, and hot melt can be taken in accordance with the characteristics of the paint.

5) Standards;

The electrode performance of the biological electrode 1 after assembly must satisfy the standard, AAMI/ANSI-EC-12: Pregelled ECG Disposable Electrodes (1982).

In the first embodiment, instead of the sponge with gel 4, an electroconductive adhesive gel 4A formed in the size equivalent to the pad portion 3 may be provided in the biological electrode 1A as shown in FIG. 3. In this case, since the adhesion is provided by the electroconductive adhesive gel 4A, the electrode can be secured adhesively to the skin by the electroconductive adhesive gel 4A, so the adhesive property of the pad portion 3 is unnecessary.

In the biological electrode 1A as shown in FIG. 3, like parts are indicated by the same numerals as shown in FIG. 2, and are not described.

Second Embodiment

FIG. 4 shows a second embodiment of the invention.

In a biological electrode 30 as shown in FIG. 4, an electrode element 31 is formed with an electroconductive layer 33 on the side of a film-like substrate 32 in contact with a living body (i.e., on the lower side in FIG. 4), and can be thin with an electroconductive gel 34 on this electroconductive layer 33.

The substrate 32 in this embodiment can be also constituted of a non-woven fabric made of a biodegradable material. In this way, since the substrate 32 is constituted of the non-woven fabric, the biological electrode 30 is so flexible as to reduce uncomfortableness in attaching and have good air permeability.

(4) A manufacturing method of the film-like electrode element 31 will be described below.

1) molding the electrode element 31;

The biodegradable materials of the film of polyhydroxy carboxylic acids such as polylactic acid, aliphatic polyester (e.g., polybutylenesuccinate (PBS), polybutylenesuccinate adipate (PBSA), and polyethylenesuccinate (PESu)), or polycaprolactone (PCL) or the non-woven fabric of cellulose or chitosan may be used as the substrate of the electrode element 2.

2) Coating the electroconductive paint on the surface of the electrode element 31;

The electroconductive paint is coated on the surface of the substrate 32 to provide the electroconductivity as the biological electrode 30.

The kinds of electroconductive material to be added to the electroconductive paint include carbon black, silver, and silver/silver chloride.

Carbon black may be acetylene black or furnace black.

When the substrate 32 is a non-woven fabric, the electroconductive paint is coated on the surface of the substrate 32, or infiltrated into the substrate 32 to provide the electroconductivity as the biological electrode 30.

3) Coating the non-polarized elecroconductive paint on the electrode paste contact face of the electrode element 31;

To further enhance the performance of the biological electrode element, an electroconductive paint of silver/silver chloride as the electroconductive material may be coated at least at a part in contact with the electrode paste or the electrode gel on the electrode element having electroconductivity, if necessary.

4) Standards;

The electrode performance of the biological electrode after assembly must satisfy the standard, AAMI/ANSI-EC-12: Pregelled ECG Disposable Electrodes (1982).

In the above embodiments, the electrode element is composed of the biodegradable material. However, other constituent members in the biological electrode may be composed of the biodegradable material. The sponge 4 contains the gel in the above embodiments, but may contain the paste.

In FIG. 4, the structure of the biological electrode 30 is only illustrated in the second embodiment, but in practice, this biological electrode 30 has a lead wire 39 as shown in FIG. 5. This lead wire 39 is disposable, and made up of a water proof connector 36, a conducting wire 37 and a connector 38. Instead of the water proof connector 36, an adhesive tape or welding may be employed to secure the lead wire.

To further enhance the adhesive strength, as required, an adhesive pad 35 may be provided on the biological electrode 30 and the lead wire 39. In the biological electrode 30 as shown in FIG. 5, like constituent members are indicated by the same numerals as shown in FIG. 4, and are not described.

As described above, since the biological electrode according to the present invention is constituted by the use of the biodegradable material for the electrode element, and therefore can be decomposed completely owing to microbes in the soil or water, when wasted after the high pressure steam sterilization, for example, as medical waste, the biological electrode can be provided that causes less load on natural environment.

Also, since the biological electrode generates the small amount of heat while incinerating, the incinerator is not damaged.

Further, since polyhydroxy carboxylic acids such as polylactic acid, cellulose, polyhydroxy carboxylic acids, chitosan, aliphatic polyester (e.g., polybutylenesuccinate (PBS), polybutylenesuccinate adipate (PBSA), polyethylenesuccinate (PESu)), polycaprolactone (PCL), and starch derivatives contain no chlorine in the molecular structure, the biological electrode will not produce any environmental pollution substance such as dioxin through the incinerating process.

Since polylactic acid serves to suppress the molding, it is possible to prevent the biological electrode from molding in a moist environment in the biological electrode. Therefore, since there is no need of adding fungicide to the electrode paste, the biological electrode has no possibility of causing skin irritation due to fungicide, saving cost of fungicide.

In the invention, the case where a non-woven fabric of biodegradable material, particularly cellulose or chitosan, is employed for the film-like electrode element, it is so flexible as to follow deformation of the skin, and less delamination when attached. Further, since it is not stiff at the edge part of electrode element, the biological electrode does not cause any skin failure.

In the case of the film-like electrode element, compared with snap fastener type electrode element, the surface area is larger than in proportion to the outer shape and a large contact area with gel or paste is provided, so that the electrode element can exhibit the good performance. Also, because this film-like electrode element is porous and sweat permeable, the biological electrode keeps good performance in spite of the perspiration.

What is claimed is:

1. A biological electrode comprising:
   an electrode element having electroconductivity with respect to a living body, being made of a biodegradable material; and
   a conductive gel portion, which covers the electrode element, the gel portion being adapted to be attached on an exterior surface of the living body.

2. The biological electrode according to claim 1, wherein said biodegradable material contains at least one material selected from the group consisting of cellulose, polyhydroxy carboxylic acids, chitosan, aliphatic polyester, polycaprolactone (PCL) and starch derivatives.

3. The biological electrode of claim 2, wherein the aliphatic polyester is selected from the group consisting of polybutylenesuccinate (PBS), polybutylenesuccinate adipate (PBSA) and polyethylenesuccinate (pESU).

4. The bioligical electrode according to claim 1, wherein a matrix of said electrode element contains an electroconductive filler.

5. The biological electrode according to claim 1, wherein the surface of a matrix or substrate of said electrode element is provided with an electroconductive layer thereon.

6. The biological electrode according to claim 5, wherein said substrate is a non-woven fabric made of said biodegradable material.

7. The biological electrode according to claim 1, further comprising:

a pad portion, which supports the electrode element and the conductive gel portion.

8. The biological electrode according to claim 7, wherein said biodegradable material contains at least one material selected from the group consisting of cellulose, polyhydroxy carboxylic acids, chitosan, aliphatic polyester, polycaprolactone (PCL) and starch derivatives.

9. The biological electrode of claim 8, wherein the aliphatic polyester is selected from the group consisting of polybutylenesuccinate (PBS), polybutylenesuccinate adipate (PBSA) and polyethylenesuccinate (pESU).

10. The biological electrode according to claim 7, wherein said biodegradable material is used for all the constituent members of said biological electrode.

11. The biological electrode according to claim 7, wherein the pad portion is a non-woven fabric made of a biodegradable material.

* * * * *